Figure 1:
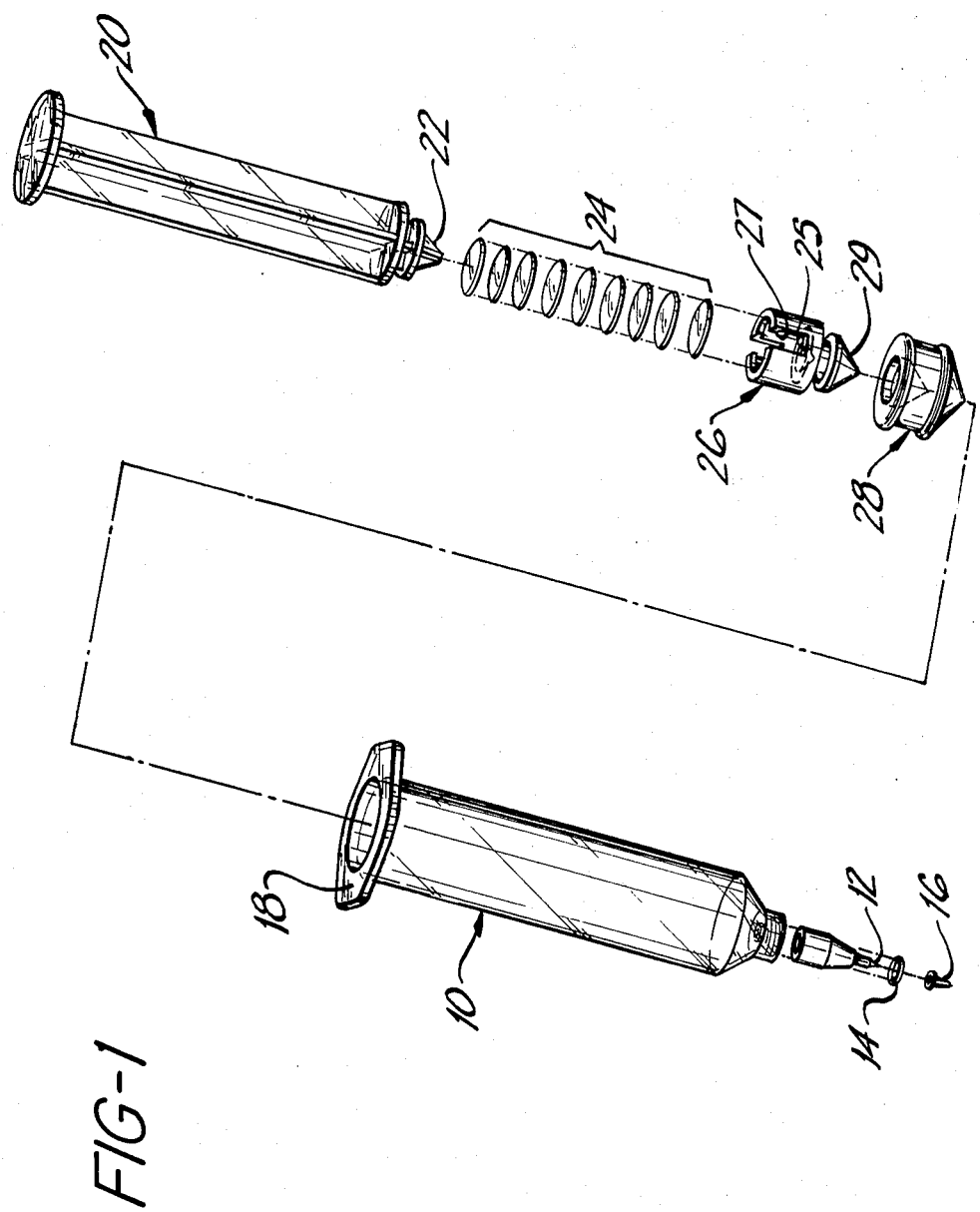

United States Patent [19]

Guess et al.

[11] Patent Number: 4,492,317
[45] Date of Patent: Jan. 8, 1985

[54] PRESSURIZING SYRINGE

[75] Inventors: Joe F. Guess; Thomas Pearce, both of Littleton, Colo.

[73] Assignee: Technicare Corporation, Solon, Ohio

[21] Appl. No.: 409,700

[22] Filed: Aug. 19, 1982

[51] Int. Cl.³ .............................................. B67D 5/06
[52] U.S. Cl. ..................................... 222/39; 73/744; 73/862.54; 92/5 R; 92/84; 604/121
[58] Field of Search ......................... 222/39, 326, 327; 221/3; 116/273, DIG. 10; 604/118, 121, 218, 222; 92/5 R, 84; 73/714, 715, 744, 862.54

[56] References Cited

U.S. PATENT DOCUMENTS

| | | | |
|---|---|---|---|
| 3,029,985 | 4/1962 | Krueger | 222/327 |
| 3,253,592 | 5/1966 | Pechmann | 604/222 |
| 4,392,589 | 7/1983 | Herold | 222/39 X |

FOREIGN PATENT DOCUMENTS 2050172 1/1981 United Kingdom ................ 604/218

Primary Examiner—Joseph J. Rolla
Assistant Examiner—Kevin P. Shaver
Attorney, Agent, or Firm—W. Brinton Yorks, Jr.

[57] ABSTRACT

A pressurizing syringe includes one or more dimple-shaped snapdomes located between the plunger and piston of a syringe assembly. When the plunger is depressed, the snapdomes will deflect at a known pressure level, giving the user a tactile and audible indication that the syringe is compressing fluid at the desired pressure. A method for using a pressurizing syringe to pressurize the fluid-filled compartment of an ultrasonic scan head is also described.

11 Claims, 2 Drawing Figures

PRESSURIZING SYRINGE

This invention relates to pressurizing syringes and, in particular, to the construction and use of a syringe-type device to controllably pressurize a fluid-filled enclosure.

In ultrasound diagnostic imaging systems an ultrasonic transducer is used to scan the tissue of a patient who is being imaged. The ultrasonic transducer is generally mounted in a fixture known as a scan head, and is contained in a fluid-filled chamber. The acoustic fluid in the chamber has a high sonic conductivity, and is used to couple sonic energy between the transducer and the patient over a path of a desired sonic impedance.

A problem frequently encountered in fluid-filled scan heads is the formation of bubbles. If air bubbles are allowed to develop in the fluid, they can adhere to the surface of the transducer or mirror in the chamber, if one is used. These bubbles will interfere with the flow of ultrasonic energy, since they act as low impedance points in the acoustic fluid which tend to scatter ultrasonic energy. The formation of bubbles can thus result in the production of a distorted ultrasonic image by the system.

The manner in which the air bubbles can enter the chamber are many. One common way for air bubbles to enter the chamber is through leaking seals during temperature cycling. If a seal in the fluid-filled chamber is not fluid-tight and the scan head is warmed, the fluid will expand, increase in pressure, and leak out through the seal. When the scan head cools, the fluid will contract, thereby producing a negative pressure in the chamber relative to atmospheric which can draw air into the chamber.

The problem of bubble formation due to temperature cycling may be greatly alleviated by pressurizing the fluid-filled chamber of the scan head. A scan head with a pressurized chamber is shown in U.S. patent application Ser. No. 352,910, filed Feb. 26, 1982 by Bayard G. Gardineer and entitled "LOW PRESSURE HEAD FLUID RESERVOIR." A scan head illustrated in this patent application contains a one-way valve in the side of the fluid-filled chamber through which the chamber can be initially filled and subsequently refilled. By initially pressurizing the chamber at a pressure greater than atmospheric, the chamber can go through temperature cycling and fluid can leak through the chamber seals as before. But if the pressure within the chamber is still greater than atmospheric pressure after the scan head has cooled, the pressure differential will prevent any drawing of air into the chamber. Air bubble formation due to temperature cycling is thereby prevented.

However, once the scan head is in the hands of a user, it is necessary to provide a means whereby the user can repressurize the scan head chamber from time to time without the need for a service call to the manufacturer. It would be possible, for instance, to supply the user with a pump and pressure gauge so that the scan head could be pumped with fluid until the gauge reaches the desired pressure. But such a system would be both complicated and expensive. Thus, it is desirable to provide a means for repeatedly pressurizing the scan head to a known pressure, including apparatus which is both simple and inexpensive.

In accordance with the principles of the present invention, a pressurizing syringe is provided which is suitable for pressurizing an enclosure to a predetermined pressure level. A syringe contains one or more snapdomes which "snap" at a predetermined pressure when the syringe plunger is depressed. The snapdomes thereby provide the user with both a tactile and audible signal when the syringe is delivering fluid at a desired pressure. The pressurizing syringe with snapdomes is simple, inexpensive, easy to use, and a familiar looking item to medical personnel.

in accordance with the principles of a further aspect of the present invention, a pressurizing syringe with a pressure-sensitive snapdome is used to pressurize the fluid-filled chamber of an ultrasound scan head. The syringe is first filled with acoustic fluid. The needle is then inserted into a fill port of the scan head, and is seated so as to be relatively fluid-tight. The plunger is then depressed until the syringe clicks. The plunger pressure is maintained at approximately the click pressure until the fluid pressure within the scan head stabilizes. If desired, the syringe can be clicked several times to ensure that the proper pressure is being maintained during the stabilizing period. After the fluid pressure has stabilized, the syringe is withdrawn from the fill port and the scan head is ready for use.

Figure 2:
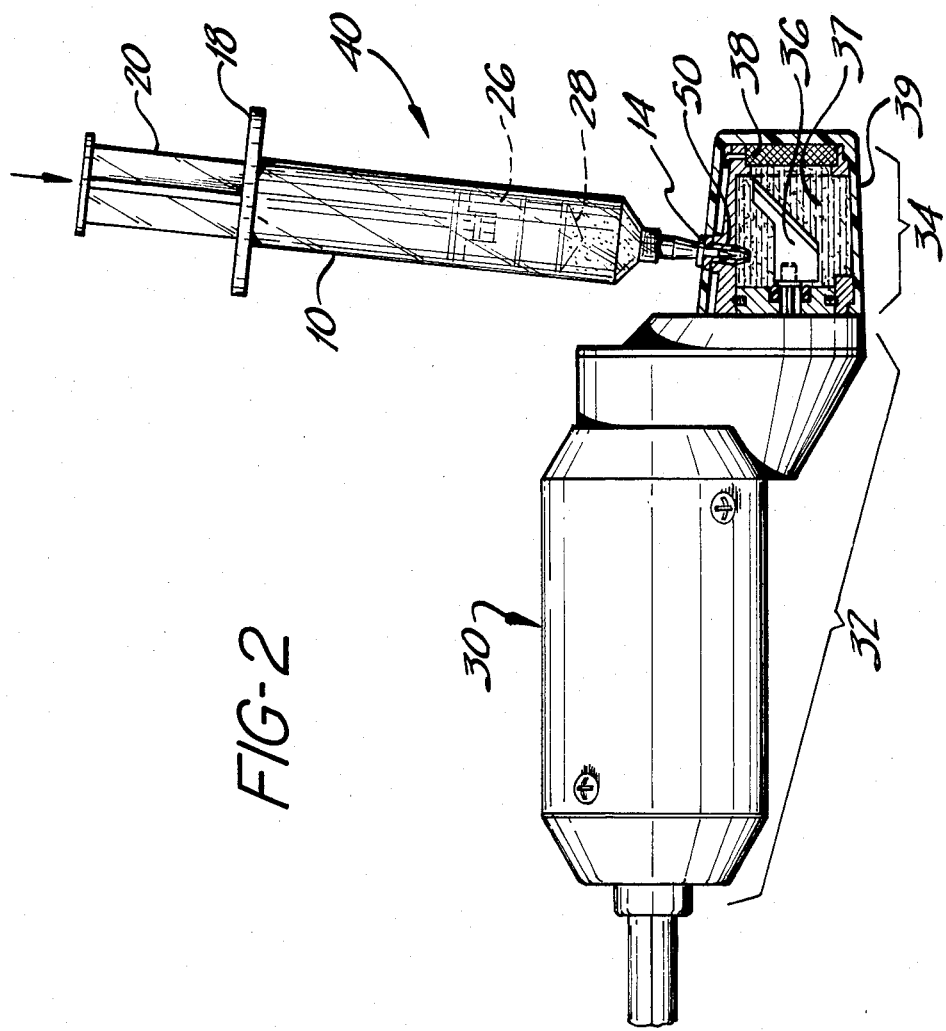

In the drawings:

FIG. 1 illustrates an exploded view of a pressurizing syringe constructed in accordance with the principles of the present invention; and FIG. 2 illustrates the pressurizing of an ultrasound scan head by a syringe with a pressure-sensitive snapdome in accordance with the principles of the present invention.

Referring to FIG. 1, an exploded view of a pressurizing syringe constructed in accordance with the principles of the present invention is shown. In FIG. 1 the hollow outer or barrel section 10 of the pressurizing syringe has an opening at the proximal end 18 to admit the plunger assembly shown at the right side of the FIGURE. A hollow needle 12 is mounted at the distal end of the barrel section 10. Just above the needle 12 is an O-ring 14. A needle cover 16 is used to protect the needle 12 when the pressurizing syringe is not in use.

The plunger assembly of the pressurizing syringe is shown at the right of the FIGURE. A plunger 20 includes a generally pointed knob end 22. When assembled, the pointed knob is located inside a hollow snapdome enclosure 26, and is held there by an interior lip 27 of the enclosure. The assembly includes a number of dimpled snapdomes, shown at 24, which are stacked in the bottom of the enclosure 26 when the pressurizing syringe is fully assembled. Notches 25 are located on either side of the enclosure 26, one of which is shown in the FIGURE. The notches permit easy insertion of the stacked snapdomes into the enclosure, as well as flexing of the lip portion 27 when the knob 22 is engaged in the enclosure. Another generally pointed knob 29 is located at the bottom of the enclosure 26 and is used to engage a piston 28.

The pressurizing syringe of FIG. 1 is seen to contain conventional parts of a hypodermic syringe, except for the snapdomes 24 and the snapdome enclosure 26. The snapdomes in the enclosure, in combination with the downward pressure exerted on the snapdomes by the knob 22, enable the assembled pressurizing syringe to provide fluid at a known pressure. With the needle cover in place and a fluid located in the barrel section 10, the plunger assembly is inserted into the barrel section 10. As the plunger 20 is depressed, the knob 22 exerts a force against the stacked snapdomes, which force is in turn transferred to the fluid. As this force is increased, a point will be reached at which the snapdomes deflect, or "snap", emitting a popping sound and giving a tactile indication that a predetermined force level has been reached. Since the force needed to deflect the snapdomes is known, the force exerted on the fluid is predictable.

For instance, the pressure inside the barrel 10, neglecting friction, is given by the ratio of the force applied to the plunger divided by the cross-sectional area of the syringe. This is approximated by the area of the piston 28, which in an actual embodiment of the present invention was measured as 0.44 square inches. The force nominally exerted by each snapdome before it snapped was found to be 0.66 lb. Therefore, each snapdome should "snap" under a force of 0.66 lb. divided by 0.44 square inches, or 1.5 psi. However, it was found that the pointed knob, which concentrates the applied force over only a small area of the snapdomes, causes the snapdomes to deflect at a lower than predicted force of 1.37 psi.

Thus, if it is desired to pressurize the fluid in the syringe to a level of 1.37 psi, only one snapdome would be required in the enclosure 26. By stacking additional snapdomes in the enclosure, the forces required to deflect the snapdomes additively combine. For example, when six snapdomes are used, 4 lb. of pressure is required before the snapdomes snap. By dividing the 4 lb. force by the piston area of 0.44 square inches, a predicted fluid pressure of 9.1 psi is calculated. When the pointed knob is further taken into consideration, the predicted value becomes 8.2 psi. A six snapdome assembly was built and tested, and was found to produce a measured pressure of 7.8 psi, which is within five percent of the predicted value.

FIG. 2 shows a scan head 30 being pressurized by a pressurizing syringe 40 in accordance with the principles of the present invention. The scan head 30 is of the type shown and described in the aforementioned U.S. patent application Ser. No. 352,910, and in U.S. Pat. No. 4,330,874. The scan head 30 includes a first section 32, including an enclosed motor and drivetrain. The motor and drivetrain are connected to oscillate a mirror 36, which is contained in a fluid-filled chamber 37. As the mirror 36 oscillates, it translates ultrasonic energy between an ultrasonic transducer 38 and an aperture 39 in the bottom of the transducer section 34 of the scan head.

A duck billed check valve 50 is shown located at the top of the transducer section 34. The check valve 50 provides a fill port for the transducer section whereby acoustic fluid may be injected under pressure into the chamber 37.

In an actual embodiment of the scan head shown in FIG. 2, it has been found desirable to maintain the acoustic fluid pressure at around 10 psi to prevent air bubble formation in the chamber. Furthermore, it is recommended that the scan head be repressurized approximately once a week to ensure that small leaks do not lead in time to the development of negative fluid pressures. The pressurizing syringe of FIG. 1 satisfies these requirements. A hypodermic syringe is readily capable of delivering a pressure of 50 psi, which would rupture the seals in the scan head. But by using the pressurizing syringe with the snapdomes, the user is notified by the "snap" when the desired pressure has been reached. Moreover, the pressurizing syringe is easy to use, so that weekly repressurizations do not become overly inconvenient.

In order to deliver the desired fluid pressure of about 10 psi, seven of the above-described snapdomes, each snapping at approximately 0.67 lb., are required. The force required to overcome the cumulative resistance of the seven snapdomes is approximately 4.67 lb. Dividing this force by the piston area of 0.44 square inches yields a calculated pressure of 10.6 psi. As explained above, the relatively pointed knob 22 will cause the snapdomes to deflect at a pressure lower than the calculated pressure, about 9.6 psi. This has been found to be acceptable for the embodiment of the scan head of FIG. 2.

If the user has not used the pressurizing syringe previously, it may be desirable to test the syringe so as to acquire a sense of the required plunger pressure. This may be done by leaving the needle cover on the assembled syringe and pressing the plunger. The user can then note the force being exerted when the snapdomes click at about 10 psi of pressure.

Once the user has gained some familiarity with the pressurizing syringe, the pressurizing sequence may be initiated. Since the purpose of pressurizing is to keep air out of the chamber 37, it is advisable to first bleed air out of the syringe. This is done by removing the needle cover 16 and lightly pressing the plunger 20 until a small amount of fluid is emitted.

To pressurize the scan head, the needle 12 is inserted into the check valve 50. The plunger is then pressed slowly to fill the inside of the valve with fluid, thereby displacing all air from the valve. Once the valve has been filled, the syringe is pressed down firmly so as to seat the O-ring 14 at the top of the check valve 50, as shown in FIG. 2. The plunger is then depressed until the snapdomes click. The plunger may then be released slightly to feel the return click. The acoustic fluid should now be flowing through the check valve 50 and into the chamber 37.

The plunger pressure is maintained at approximately the click pressure for 45 to 60 seconds to allow the fluid pressure to stabilize. While the pressure is stabilizing the user may alternately press and relax the plunger slightly so as to hear the snapdome click and return click. This provides a positive indication that the syringe is maintaining the desired fluid pressure during stabilization.

After allowing sufficient time for pressure stabilization, the plunger pressure is released and the syringe is withdrawn from the check valve. Excess fluid may then be wiped from the scan head, readying it for use, and the needle cover put back in place on the syringe.

What is claimed is:

1. In a syringe, including a hollow barrel section which contains a plunger assembly, a needle located at the distal end of said barrel section, and a fluid compartment located between said plunger assembly and said needle, wherein said plunger assembly includes a plunger, and a piston located between said plunger and said fluid compartment; the improvement comprising:
   a snapdome located between said plunger and said piston, said snapdome deforming upon the attainment of a predetermined pressure within the fluid compartment to provide an audible indication thereof to a user.

2. The arrangement of claim 1, further comprising:
   a snapdome enclosure for housing said snapdome, located between said plunger and said piston, and including a first, open end for engaging said plunger and a second end for engaging said piston.

3. A syringe for pressurizing a fluid to a predetermined level comprising:

a hollow barrel section having a first aperture at one end, and a second aperture at the other end through which said fluid may be emitted;

a plunger assembly suitable for insertion in said first aperture of said barrel section, said plunger including a proximal end defining a fluid chamber between said proximal end and said second aperture when inserted in said barrel section; and a snapdome located within said barrel section and having a normal shape, and responsive to the attainment of a fluid pressure within said fluid chamber which is a given increment above ambient pressure, whereupon said snapdome is deflected to a shape other than its normal shape and audibly indicates to a user the attainment of said given increment above ambient pressure.

4. The arrangement of claim 3, wherein said audible indication of said snapdome when deflected is an audible click.

5. The arrangement of claim 3, wherein said snapdome also produces a tactile indication when deflected, thereby indicating the attainment of said given increment above ambient pressure.

6. The arrangement of claim 3, wherein a plurality of snapdomes are located within said barrel section and are responsive to the attainment of a fluid pressure within said fluid chamber which is a given increment above ambient pressure.

7. The arrangement of claim 3, wherein said plunger assembly includes a piston located at the proximal end thereof and a plunger located between said piston and said first aperture when said assembly is inserted in said barrel section; wherein said snapdome is located between said piston and said plunger.

8. A syringe for pressurizing a fluid to a predetermined level comprising:

a hollow barrel section having a first aperture at one end suitable for receiving a plunger assembly, and a second aperture at the other end through which said fluid may be emitted; and a plunger assembly suitable for insertion in said barrel section, including a plunger having a proximal end which is to be inserted into said barrel section, a piston which is to be inserted in said barrel section so as to be located between said proximal end of said plunger and said second aperture and forming a fluid seal with the inner wall of said barrel section to thereby define a fluid chamber between said piston and said second aperture; and a snapdome located between said proximal end of said plunger and said piston, said snapdome deforming upon the attainment of a predetermined pressure within the fluid chamber to provide an audible indication thereof to a user.

9. The arrangement of claim 8, wherein said plunger further includes a substantially pointed knob located at said proximal end thereof.

10. The arrangement of claim 9, further comprising:

a snapdome enclosure for housing said snapdome, including a first, open end for engaging said plunger knob, and a second, knob-shaped end for engaging said piston.

11. The arrangement of claims 8 or 10, further comprising:

a hollow needle connected to said second aperture; and an O-ring located about said second aperture.

* * * * *